United States Patent [19]

Landymore et al.

[11] Patent Number: 4,836,204
[45] Date of Patent: Jun. 6, 1989

[54] METHOD FOR EFFECTING CLOSURE OF A PERFORATION IN THE SEPTUM OF THE HEART

[76] Inventors: Roderick W. Landymore, R.R. #2, Spruce Court, Three Fathom Harbour, N.S., Canada, B0J 1N0; Allan E. Marble, 6366 South Street, Halifax, N.S., Canada, B3H 1T9

[21] Appl. No.: 69,870

[22] Filed: Jul. 6, 1987

[51] Int. Cl.[4] .................. A61M 25/00; A61B 17/04
[52] U.S. Cl. .................. 128/334 R; 604/53; 604/101; 128/325
[58] Field of Search .......... 128/334 R, 334 C, 325; 604/101, 51–53

[56] References Cited

U.S. PATENT DOCUMENTS

| | | | |
|---|---|---|---|
| 3,848,602 | 11/1974 | Gutnick | 604/101 |
| 3,874,388 | 4/1975 | King et al. | 128/334 C |
| 3,952,742 | 4/1976 | Taylor | 604/101 X |
| 4,090,518 | 5/1978 | Elam | 604/101 |
| 4,180,076 | 12/1979 | Betancourt | 604/101 |
| 4,198,981 | 4/1980 | Sinnreich | 604/101 |
| 4,327,736 | 5/1982 | Inoue | 604/101 |
| 4,329,993 | 5/1982 | Lieber et al. | 604/101 |
| 4,351,342 | 9/1982 | Wiita et al. | 604/43 |
| 4,484,579 | 11/1984 | Meno et al. | 604/101 X |

FOREIGN PATENT DOCUMENTS

| | | |
|---|---|---|
| 554527 | 3/1958 | Canada . |
| 805931 | 2/1969 | Canada . |
| 1109750 | 9/1981 | Canada . |
| 1178868 | 12/1984 | Canada . |
| 1181311 | 1/1985 | Canada . |
| 3227575 | 7/1982 | Fed. Rep. of Germany . |

OTHER PUBLICATIONS

Rashkind, W. Transcatheter treatment of congentail heart disease, Circulation 67:711–716, 1983.
Mills, N., Vargish, T., Kleinman, L., Bloomfield, D., Reed, G., Balloon closure of ventricular septal defect, Circulation Suppl. I.111–114, 1971.

Primary Examiner—Dalton L. Truluck
Attorney, Agent, or Firm—Killworth, Gottman Hagan & Schaeff

[57] ABSTRACT

A novel double-balloon septal defect occlusion catheter which is used in conjunction with a unique surgical procedure to temporarily close septal perforations, particularly spontaneous ventricular septal perforations following acute myocardial infarction, without the need for open heart surgery, thus permitting the patient's condition to stabilize and permitting elective surgical closure of the defect at a later date.

8 Claims, 3 Drawing Sheets

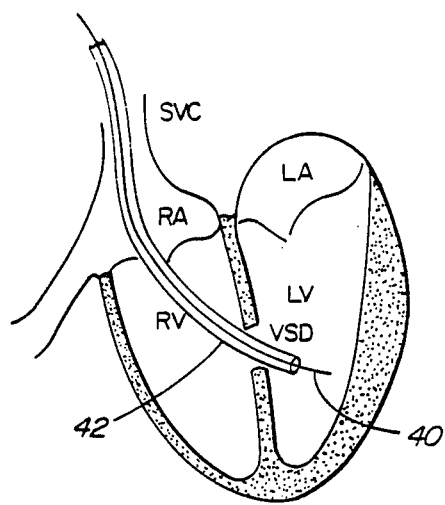
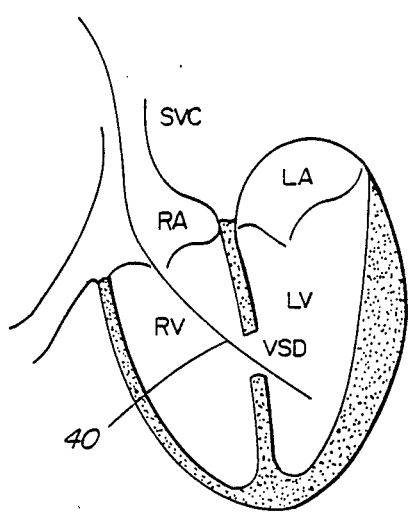
FIG. 11					FIG. 12
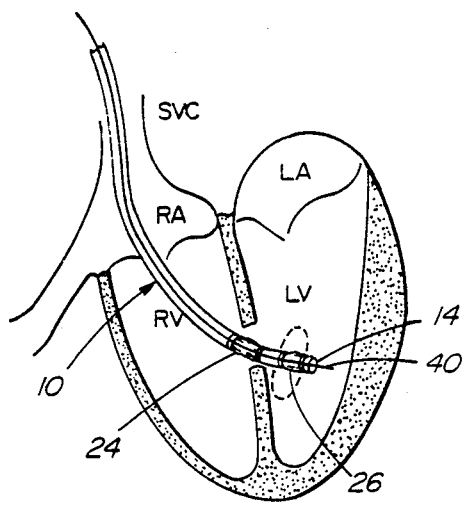
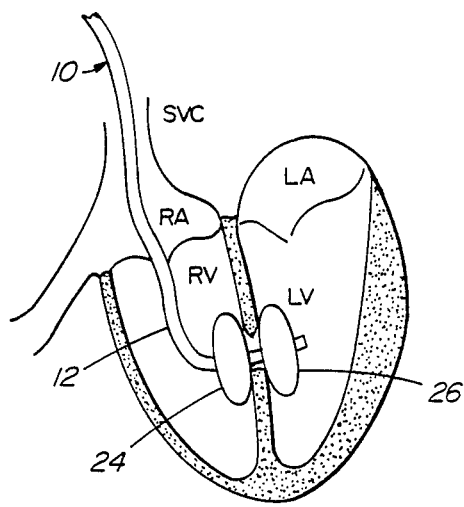
FIG. 13					FIG. 14

METHOD FOR EFFECTING CLOSURE OF A PERFORATION IN THE SEPTUM OF THE HEART

BACKGROUND OF THE INVENTION

This invention relates to a method for effecting closure of a perforation in the septum, particularly the interventricular septum of the human heart.

Spontaneous perforation of the interventricular septum after acute transmural myocardial infarction is observed in one to two per cent of patients. The septal perforation usually occurs within the first two weeks following the infarction, and is associated with a large left to right intracardiac shunt which results in low cardiac output and cardiac decompensation. This complication of acute myocardial infarction is invariably fatal and has been associated with an 85 per cent mortality within the first two months. Operative intervention to close the defect has not met with widespread success. Operative mortality has been reported to range from 34–82 per cent and is influenced by the timing of the operation with improved survival related to delayed operative intervention. Unfortunately, the great majority of patients deteriorate rapidly after septal perforation and require emergency closure of the defect. Hence, there is a great need for a technique for effecting closure of the ventricular septal defect and which at the same time avoids the need for open heart surgery immediately following an acute myocardial infarction.

SUMMARY OF THE INVENTION

The present invention provides a unique surgical method which is capable of closing the septal defect while avoiding the need for immediate open heart surgery, thus affording the potential for a substantial reduction in the mortality rate commonly associated with this type of defect.

In particular, the present invention makes use of a novel double-balloon septal defect occlusion catheter which is used in conjunction with a unique surgical procedure to temporarily close septal perforations, particularly spontaneous ventricular septal perforations following acute myocardial infarction without the need for open heart surgery, thus permitting the patient's condition to stabilize and permitting elective surgical closure of the defect at a later date.

In order to carry out the method of the invention there is described herein a catheter for effecting closure of septal perforations including an elongated flexible shaft having a plurality of lumens commencing adjacent the proximal end and with first and second expandable balloons located adjacent the distal end of the shaft. These balloons are, in the unexpanded condition, sufficiently small as to permit passage of the distal end portion of the catheter through a blood vessel and into the heart and thence through the perforation in the septum thereby to position the balloons on opposing sides of the septum. The balloons are designed so that in the inflated condition these balloons are in a snug leak-resistant engagement with the opposing walls of the septum all around the perforation. Each of the balloons has a lumen respectively associated therewith so as to permit the balloons to be inflated and deflated independently of each other. Furthermore, in the preferred embodiment to be described hereinafter, a third lumen extends from the proximal end to and through the distal end of the catheter to allow for passage therealong of an elongated guidewire for introduction of the catheter into the heart.

The above-noted balloons are spaced apart along the flexible shaft by a predetermined distance so that the septum of the heart can be snugly accommodated between the balloons when inflated. The catheter should have a total length at least sufficient as to extend from a point within the left ventricle of the heart to a point in the patient's neck adjacent the internal or external jugular vein.

Although various balloon shapes can be used, such as spheroidal shapes, it is preferred that the balloons have somewhat flattened or discoid shapes when inflated, thereby to minimize the volumes taken up by such balloons within the ventricles.

The proximal end of the catheter is made so that it can be buried in the subcutaneous tissues adjacent the insertion site. Preferably, the first and second lumens associated with the above-noted balloons are colour coded and are provided with self-seal needle piercable inlet ports thereby to allow for the controlled injection of fluid into the balloons to expand them. The third lumen is provided with a threaded port which can be ultimately capped with a threaded plug once the closure procedure has been completed.

The method for effecting closure of septal perforations in accordance with the invention includes the steps of providing an elongated catheter having first and second expandable balloons located adjacent the distal end of the catheter shaft as described above. The distal end of the catheter, with the balloons deflated, is passed through a large blood vessel from the exterior of the patient's body and into the heart and thence through the perforation in the septum thereby to position the deflated balloons on opposing sides of the septum. The balloons are then inflated thereby to cause them to snugly engage the opposing walls of the septum all around the perforation thereby to prevent leakage through such perforation.

In the preferred form of the method the incision site is on the patient's neck, preferably over the right internal jugular vein. The catheter is ultimately passed along this jugular vein and into a ventricle of the heart and thence through the perforation in the septum as described above.

In accordance with a method aspect of the invention, that balloon which is most closely adjacent the distal end of the catheter is inflated first and brought into close engagement with the wall of the septum, following which the other balloon is inflated to cause the opposing walls of the septum to be snugly engaged as described above.

As a further feature of the method defined herein, a steerable catheter is initially introduced via the large vein noted above into the heart and it is passed through the perforation into the septum. A guidewire is then fed through the steerable catheter with the latter being thereafter removed, following which the first mentioned catheter is fed along the guidewire into the heart to position the balloons on opposing sides of the septum as described above.

Further in accordance with the method, contrast medium is introduced into the balloons to effect the inflation of same and so that the inflation and the positioning of the balloons may be observed by fluoroscopy or the like. A contrast medium is also passed through a third lumen of the catheter into the heart to enable any leakage around the inflated balloons to be detected by fluoroscopy.

Once the surgeon is satisfied that the septal perforation has been adequately closed, the proximal end of the catheter is buried in the patient's subcutaneous tissues adjacent the insertion site and the catheter is allowed to remain in the patient until the patient's condition has stabilized, following which the septal perforation can be permanently closed by way of open heart surgical techniques.

Further features and advantages of the invention will become apparent from the following detailed description of a preferred form of the invention taken in conjunction with the accompanying drawings.

BRIEF DESCRIPTION OF THE VIEWS OF DRAWINGS

FIG. 1 is a side elevation view of a catheter for use in accordance with the invention, a portion of the septum being shown in dashed lines;

FIGS. 2 and 3 are cross-section views taken along lines 2—2 and 3—3 of FIG. 1;

FIGS. 4 and 5 are section views through the inflated balloons taken along lines 4—4 and 5—5 of FIG. 1;

FIGS. 8 through 14 illustrate the several steps involved in the positioning of the catheter in the heart thereby to occlude a ventricular septal defect.

DETAILED DESCRIPTION OF PREFERRED EMBODIMENTS AND METHODS

Figure 1:
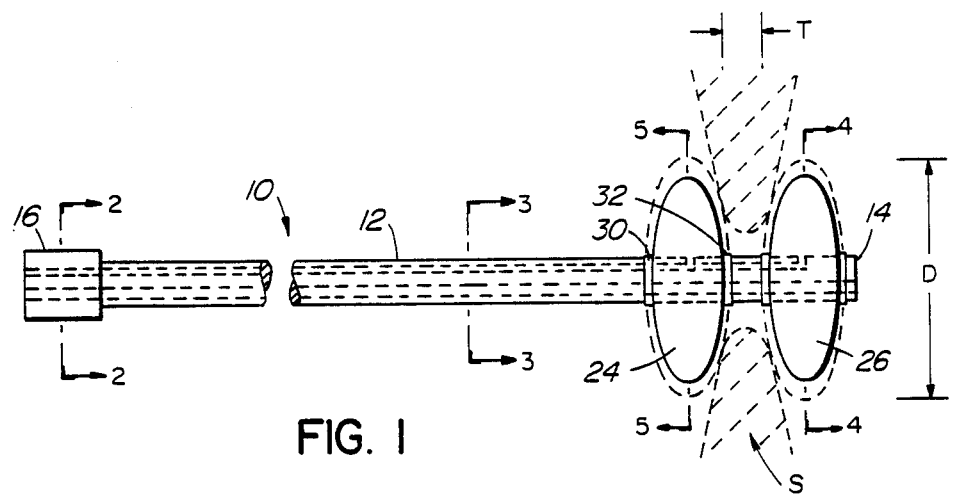
Figure 2:
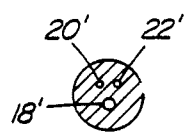
Figure 3:
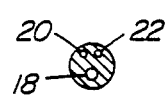
Figure 4:
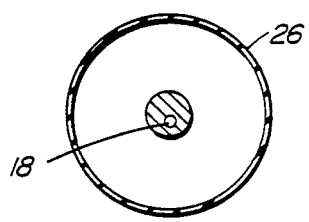
Figure 5:
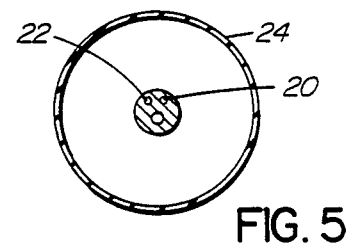

Referring now to the drawings, particularly FIGS. 1 through 5, there is shown a catheter 10 for use in accordance with the invention, the catheter including an elongated shaft 12 formed of a radiopaque, sterilizable, firm, flexible, material such as polyethylene and terminating at its distal end in a tip portion 14 and at its proximal end in an enlarged section 16. Catheter shaft 12 has three lumens extending from the proximal end of the catheter, one lumen 18 being relatively large, e.g. about 2 mm. in diameter, while the remaining two lumens 20, 22 are relatively smaller, e.g. about 1 mm. in diameter. The larger lumen 18 extends the complete length of the catheter 10 and allows the passage of the catheter over a guidewire, the latter being referred to later on in the description of the surgical procedure. The remaining two smaller lumens 20 and 22 extend from the proximal end of the catheter to the interiors of the two somewhat discoid shaped balloons 24 and 26 which are located toward the distal end of the catheter shaft 12. More specifically, one of the smaller lumens, i.e. lumen 22, extends to the interior of the nearest or proximal balloon 24, while the other small lumen 22 extends to the interior of the distal balloon 26. These two small lumens 20 and 22 are used to inject radiopaque dye into each of the balloons thereby to inflate the same.

The enlarged proximal end portion 16 is provided with two input ports 20' and 22' communicating respectively with lumens 20 and 22. These two input ports, which are used for injecting radiopaque dye into the balloons, are not open ports but rather are closed with needle piercable self-seal latex. The injection of radiopaque dye is accomplished by plunger a No. 18 gauge needle, connected to a syringe, through the latex seal.

The two self-seal ports 20', 22', are colour-coded in order that the clinician is readily able to identify one port from another. The larger (2 mm.) diameter port 18' which communicates with lumen 18 in the catheter shaft is a Luer Lok (threaded female) which is capped with a threaded plug once the guidewire has been removed as will be described in further detail hereinafter.

The balloons 24 and 26 are typically made of latex and preferably are constructed in such a manner that when they are inflated they assume somewhat discoid shapes. The discoid shape is preferred, rather than the more conventional spherical shape, in order to minimize the volumes taken up by the inflated balloons within the two ventricles of the heart. The discoid shape can be realized fairly readily by selecting the thickness and/or elastic modulus of the balloon material such that the physical properties are different for the portions of the balloon located within the first one-half to three-quarters of its fully inflated diameter, as compared to the remaining radially outermost extremeties of the balloon. This variation in the physical properties of the two portions of the balloon cause it, when inflated, to be more elastic at its outer extremity than in the radially inner portions of the balloon which are closest to the catheter shaft 12. Manufacturers of catheters have, for many years, been making various shapes and sizes of balloons and it is believed that discoid shaped balloons as illustrated can be made without difficulty having regard to the description given herein.

The radially inner extremities 30, 32 of each balloon are bonded to the exterior surface of the catheter shaft 12 in spaced apart relationship as illustrated by way of a suitable adhesive material well known, per se, in the art.

Insofar as dimensions are concerned, the shaft 12 of the catheter is typically about 40 centimeters long and about 4 millimeters in diameter. The catheter length must be sufficient as to enable it to extend from a point within the left ventricle, through the septal perforation, and outwardly of the heart and up through a large vein, e.g. the internal jugular vein, and thence outwardly of the incision site in the patient's neck. A catheter about 40 centimeters long is considered to be adequate for most adult patients and should the catheter be slightly too long, the excess can be buried in the subcutaneous tissues adjacent the incision site.

Figure 7:
FIG. 7 is a view of the distal end portion of the catheter of FIG. 1 but illustrating the balloons in the deflated condition.

The balloons 24 and 26 must be capable of expanding from the fully collapsed condition shown in FIG. 7 to the fully expanded positions illustrated in FIG. 1. In the fully collapsed condition the two latex balloons lie close to the catheter shaft with their outside diameters only being a few millimeters (e.g. 1 or 2 mm.) greater than the outside diameter of the catheter shaft per se thus enabling ready insertion of the distal end of catheter 10 as will be described hereafter. The distance, measured along catheter shaft 12, between the annular regions of securement 30, 32, for each balloon typically is in the order of about one centimeter. The distance T as illustrated in FIG. 1 is usually in the order of about 10 mm., for example from about 8 mm. to about 12 mm. This spacing between the annular regions where the adjacent walls of the two balloons 24 and 26 are attached to shaft 12 is chosen in accordance with the thickness of the septum S of the heart, the latter being illustrated in dashed lines in FIG. 1. The thickness of the septum in an average healthy human heart is in the order of 10 mm. In the case of a septal perforation arising from a myocardial infarction, the tissue breakdown usually causes the septal thickness to decrease toward the site of the perforation so that as seen in cross-section, the septum walls have the somewhat pointed shape illustrated in the drawing.

Since the inflated balloons 24, 26 must come into snug leak resistant engagement with the opposing walls of the septum all around the perforation, the balloons must be capable of being inflated to a diameter which is substantially greater than the maximum diameter of a perforation likely to be encountered. Since septal perforations having a diameter of 25 millimeters are not uncommon, the balloons must be capable of being inflated to diameters in the range of 35–45 mm. without difficulty.

Figure 6:
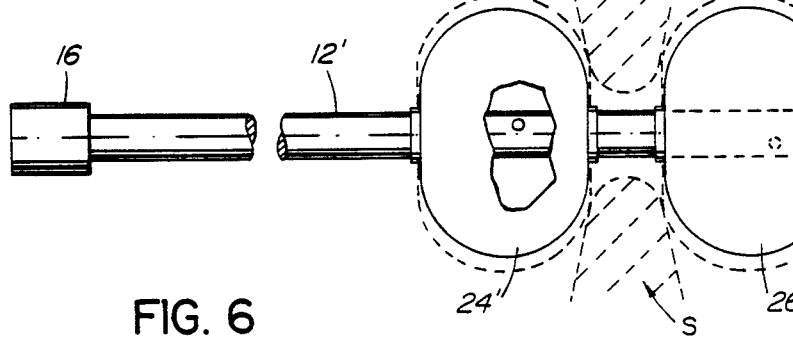
FIG. 6 is a view similar to the view of FIG. 1 but illustrating a somewhat different balloon shape.

Referring now to the embodiment illustrated in FIG. 6, a modified balloon arrangement is illustrated. In this arrangement, the balloons 24', 26', are of a somewhat more spherical or spheroidal shape. These balloons are also illustrated as being in close engagement with opposing walls of the septum S all around the site of the perforation. The same considerations apply to dimensions T and D as described above. A disadvantage however of the embodiment shown in FIG. 6 is that the balloons 24', 26' occupy relatively greater volumes within the two ventricles of the heart than do the balloons 24, 25, illustrated in FIG. 1. This may not provide to be a serious disadvantage in many cases, especially where ventricular volume is relatively great in comparison with the volumes occupied by the two spheroidal balloons. However, in cases where ventricular volume is limited (as in the case where a child is involved) the use of the more discoid shape illustrated in FIG. 1 may be necessary.

It was noted previously that the balloons may be made from latex. However, other medically acceptable elastic rubber or rubber-like synthetic materials such as Silastic may be used.

Surgical Technique

The patient is transported to the Cardiac Catheterization Laboratory for ventriculography to confirm the diagnosis of septal perforation, to determine the size and position of the perforation and for insertion of the ventricular septal defect occlusion catheter. A pig-tailed catheter is inserted through the femoral artery and positioned in the left ventricle with the aid of fluoroscopy. Contrast material is then injected through the lumen of the catheter to confirm the presence of a ventricular septal defect and to determine the size and position of the septal perforation. Preparations are then made for insertion of the ventricular septal defect occlusion catheter.

Figure 8:
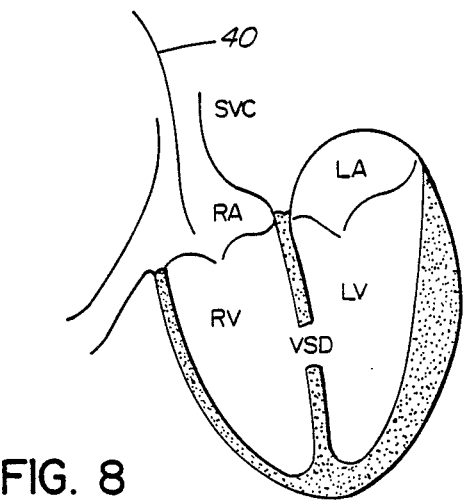
Figure 9:
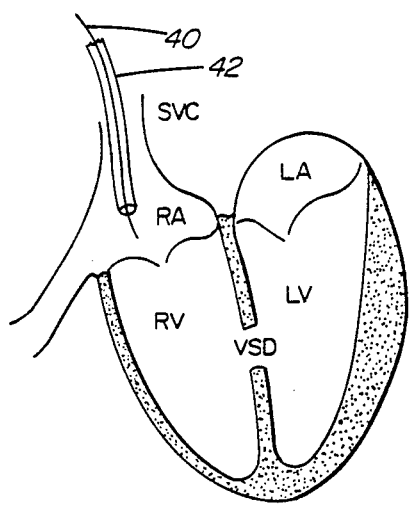
Figure 10:
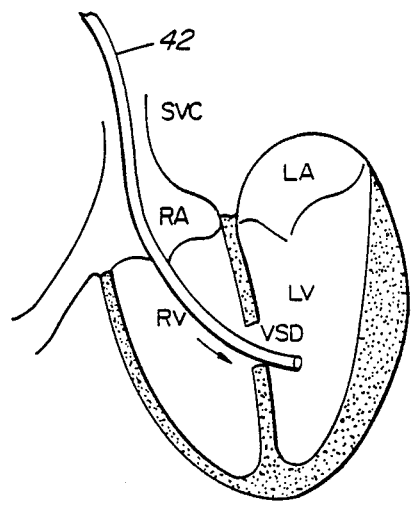

The ventricular septal defect occlusion catheter as described is designed to be inserted through a peripheral vein, preferably the right internal jugular vein. The skin overlying the right internal jugular vein is prepared for sterile surgery and a 14 gauge needle is inserted into the jugular vein after anaesthetizing the skin and subcutaneous tissues with 2 per cent Lidocaine. A flexible guidewire 40 is passed through the lumen of the needle and positioned in the right atrium (RA) (see FIG. 8). The needle is then removed, leaving the guidewire in place. A steerable catheter 42, e.g. a No. 10 French steerable catheter (Cat.#G.B./10/30A by Medi-Tech Corp., Watertown, Mass.) is passed over the guidewire 40 and positioned in the right atrium (RA) (FIG. 9). The guidewire is then removed. The tip of the steerable catheter 42 is manipulated through the tricuspid valve and into the right ventricle (RV) with the aid of fluoroscopy. The position of the ventricular septal defect (VSD) is identified by injecting contrast material through the pig-tailed catheter (not shown) which lies within the left ventricle (LV). The tip of the steerable catheter 42 is then manipulated through the ventricular septal defect VSD into the left ventricle (LV) (FIG. 10) and a flexible guidewire 40 is passed through the lumen of the steerable catheter 42 and positioned in the left ventricle LV (FIG. 11). The steerable catheter 42 is then removed and the double balloon ventricular septal defect occlusion catheter 10, as described above, with both balloons deflated, is passed over the guidewire 40 and its distal end portion positioned in the left ventricle (FIG. 13). The guidewire 40 is again removed. The distal balloon 26 of the ventricular septal defect occlusion catheter is then inflated with contrast media under fluoroscopy via lumen 20 so that the balloon 26 will completely occlude the ventricular septal defect when withdrawn against the endocardial surface of the left ventricle (LV). The proximal balloon 24 which lies within the right ventricle (RV) is then inflated with contrast media to ensure complete closure of the septal defect (VSD) and to prevent the distal balloon 26 from migrating into the left ventricle (FIG. 14). A small incision is then made over the insertion site and the proximal end portion 16 of the catheter 10 is buried in the subcutaneous tissues. The incision is closed in a sterile manner.

The catheter 10 is left in place until the patient has sufficiently recovered from the acute infarction to undergo elective open heart surgical repair of the ventricular septal defect.

The catheter described may also be adapted for closure of congenital ventricular septal defects in small children or for closure of atrial septal defects in selected patients.

The apparatus and method described above were developed in the course of a number of successful experiments on dogs. It is anticipated that the procedure as described will be applied to selected human patients in the future.

While the foregoing specification has set forth a detailed description of preferred embodiments of the invention for purposes of illustration, variation of the details herein given may be made by those skilled in the art without departing from the spirit and scope of the invention.

We claim:

1. A method for effecting transvenous closure of acquired ventricular septal perforations comprising:
   (A) providing a catheter including:
      (a) an elongated, firm, flexible shaft member having a proximal end and a distal end and defining a plurality of lumens commencing adjacent said proximal end;
      (b) a first expandable balloon and a second expandable balloon located adjacent said distal end of the shaft member, both of said balloons being constructed, arranged, and positioned relative to one another such that they are inflatable;
         (1) from an unexpanded condition wherein they have diameter(s) sufficiently small as to permit passage of the catheter distal end portion through a vein and into a ventricle of the heart and through the perforation in the septum of the heart to position said first and second balloons on opposing sides of the septum;
         (2) to an inflated condition wherein said balloons are in snug leak-resistant engagement with the opposing walls of the septum all around said perforation therein;

(c) first and second ones of said lumens communicating with said first and second balloons, respectively, to permit said balloons to be inflated and deflated independently of each other;

(B) introducing a steering catheter via said vein into the right atrium and through the tricuspid valve into the right ventricle of the heart and steering and passing the steerable catheter through the perforation in the septum, then feeding a guidewire through the steerable catheter and into the left ventricle, with the steerable catheter being thereafter removed while leaving the guidewire in position and then passing the distal end of said first mentioned catheter, with said balloons deflated along said guide wire and through said vein and into the right ventricle of the heart and thence through the perforation in the septum of the heart whereby to position the deflated balloons on opposing sides of the septum, (C) inflating the balloons thereby to cause the balloons to snugly engage the opposing walls of the septum around said defect and wherein that balloon most closely adjacent the distal end of the catheter is inflated first and brought into close engagement with the one wall of the septum following which the other balloon is inflated to bring it into close engagement with the other wall of the septum to prevent leakage through the perforation.

2. The method of claim 1 wherein contrast medium is introduced into said balloons to effect the inflation of same so that the inflation and the positioning of the balloons may be observed by fluoroscopy or the like.

3. The method of claim 1 wherein contrast medium is passed through a third lumen of the catheter into the heart to enable any leakage around the inflated balloons to be detected by fluoroscopy or the like.

4. The method of claim 1 wherein the proximal end of the catheter is buried in the patient's subcutaneous tissues and the catheter allowed to remain in the patient for a desired period of time.

5. A method for effecting closure of septal perforations comprising:

(A) providing a catheter having:
 (a) an elongated, firm, flexible shaft member having a proximal end and a distal end and defining a plurality of lumens commencing adjacent said proximal end;
 (b) a first expandable balloon and a second expandable balloon located adjacent said distal end of the shaft member, both of said balloons being constructed, arranged, and positioned relative to one another such that they are inflatable;

(1) from an unexpanded condition wherein they have diameter(s) sufficiently small as permit passage of the catheter distal end through a blood vessel and into the heart and through the perforation in the septum to position said first and second balloons on opposing sides of the septum;

(2) to an inflated condition wherein said balloons are in snug leak-resistant engagement with the opposing walls of the septum all around said perforation therein;

(c) first and second ones of said lumens communicating with said first and second balloons, respectively, to permit said balloons to be inflated and deflated independently of each other and wherein a third one of said lumens extends from said proximal end to and through said distal end to allow for passage therealong of an elongated guidewire for introduction of said catheter into the heart;

(B) introducing a steerable catheter via said blood vessel into the heart and then steering and passing the steerable catheter through the perforation in the septum, then feeding a guidewire fully through the steerable catheter, the steerable catheter being thereafter removed leaving the guidewire in place, following which the distal end of said first mentioned catheter, with said balloon deflated, is passed along said guidewire, through the blood vessel and into the chamber of the heart and thence through the perforation in the septum of the heart whereby to position the deflated balloons on opposing sides of the septum, (C) inflating the balloons thereby to cause the balloons to snugly engage the opposing walls of the septum around said defect, that balloon most closely adjacent the distal end of the catheter being inflated first and brought into close engagement with the wall of the septum following which the other balloon is inflated to prevent leakage through the perforation.

6. The method of claim 5 wherein contrast medium is introduced into said balloons to effect the inflation of same so that the inflation and the positioning of the balloons may be observed by fluoroscopy or the like.

7. The method of claim 5 wherein contrast medium is passed through the third lumen of the catheter into the heart to enable any leakage around the inflated balloons to be detected by fluoroscopy or the like.

8. The method of claim 5 wherein said proximal end of the catheter is buried in the patient's subcutaneous tissues and the catheter allowed to remain in the patient for a desired period of time.

* * * * *